United States Patent [19]

Kompis

[11] 4,076,810
[45] Feb. 28, 1978

[54] BENZYLPYRIMIDINE ANTIBACTERIAL COMPOSITION

[75] Inventor: Ivan Kompis, Oberwil, Switzerland

[73] Assignee: Hoffmann-La Roche Inc., Nutley, N.J.

[21] Appl. No.: 769,971

[22] Filed: Feb. 18, 1977

Related U.S. Application Data

[62] Division of Ser. No. 521,384, Nov. 6, 1974, Pat. No. 4,024,145.

[30] Foreign Application Priority Data

Nov. 8, 1973 Switzerland ..................... 15680/73
Oct. 24, 1974 Switzerland ..................... 14243/74

[51] Int. Cl.² ................. A61K 31/625; A61K 31/505
[52] U.S. Cl. ..................................... 424/229; 424/251
[58] Field of Search ........................... 424/251, 229; 260/256.4 W

[56] References Cited

U.S. PATENT DOCUMENTS 2,658,897  11/1953  Hitchings et al. ............ 260/256.4 N
3,341,541   9/1967  Hoffer ........................ 260/256.4 N
3,715,357   2/1973  Rey-Bellet et al. .......... 260/256.4 W Primary Examiner—Jerome D. Goldberg
Attorney, Agent, or Firm—Samuel L. Welt; George M. Gould; William G. Isgro

[57] ABSTRACT

N-oxides of benzylpyrimidines of the formula

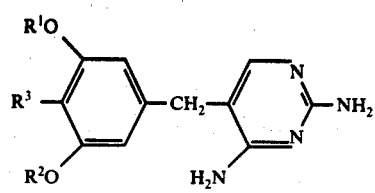

wherein $R^1$, $R^2$ and $R^3$ are as set forth hereinafter, are described. The 2,4-diamino-5-(4-bromo-3,5-dimethoxybenzyl)-pyrimidine is also described. The compounds referred to above are useful as potentiators of the antibacterial activity of sulfonamides.

1 Claim, No Drawings

BENZYLPYRIMIDINE ANTIBACTERIAL COMPOSITION

This is a division of application Ser. No. 521,384, filed Nov. 6, 1974, now U.S. Pat. No. 4,024,145, issued May 17, 1977.

BRIEF SUMMARY OF THE INVENTION

The benzylpyrimidine derivatives of the invention are compounds of the formula

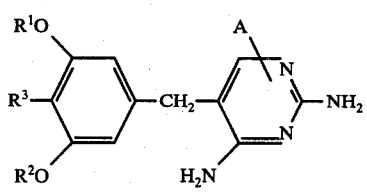

wherein $R^1$ and $R^2$, independently, are $C_{1-3}$ alkyl, $R^3$ is halogen, and A is an oxygen atom bound to one of the cyclic nitrogen atoms,
and salts thereof with pharmaceutically acceptable acids.

In another aspect, the invention relates to 2,4-diamino-5-(4-bromo-3,5-dimethoxybenzyl)-pyrimidine and salts thereof with pharmaceutically acceptable acids.

DETAILED DESCRIPTION OF THE INVENTION

The benzylpyrimidine derivatives of the invention are compounds of the formula

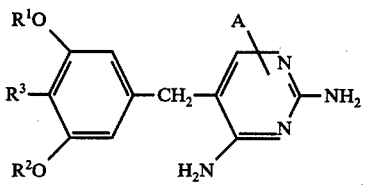

wherein $R^1$ and $R^2$, independently, are $C_{1-3}$ alkyl, $R^3$ is halogen, and A is an oxygen atom bound to one of the cyclic nitrogen atoms,
and salts thereof with pharmaceutically acceptable acids.

As used herein, the term "$C_{1-3}$ alkyl" means methyl, ethyl, propyl and isopropyl.

The N-oxides of formula I can be prepared according to known methods by treating a compound of the formula

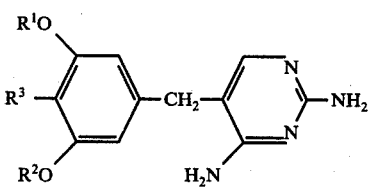

wherein $R^1$ and $R^2$, independently, are $C_{1-3}$ alkyl, $R^3$ is halogen, and A is an oxygen atom bound to one of the cyclic nitrogen atoms,
with an agent utilized to effect N-oxidation.

Especially preferred N-oxidation agents are perbenzoic acids, particularly m-chloroperbenzoic acid. The N-oxidation can be carried out, for example, in an inert solvent, for example, a chlorinated hydrocarbon such as chloroform or methylene chloride, an alkanol such as methanol or ethanol, dimethylformamide, dimethylsulfoxide, water or dioxane. The N-oxidation is conveniently carried out at a temperature in the range of from about room temperature to about the boiling point of the solvent, conveniently in the range of from about 10° C. to about 60° C. A temperature in the range of from about 10° C. to about 20° C. is preferred.

An N-oxide so obtained can be isolated from the oxidation mixture in the usual manner. When m-chloroperbenzoic acid or perbenzoic acid is used as the N-oxidation agent, it has been found to be convenient to extract the mixture obtained after treatment with the N-oxidation agent with a weak aqueous-alkaline solution, for example, aqueous sodium bicarbonate solution, to acidify the aqueous extract obtained in order to precipitate the excess acid and, after removal of the excess acid by filtration, to make the filtrate neutral or slightly basic.

The N-oxidation leads, as a rule, to mixtures of $N_1$- and $N_3$-oxides of the formulas

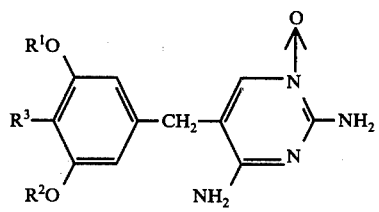

and

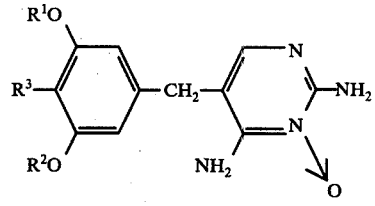

wherein, $R^1$, $R^2$ and $R^3$ are as previously described.

The separation and purification of the foregoing isomeric products can be carried out by chromatography, for example, column chromatography and/or recrystallization, preferably from polar solvents such as alkanols, water, or the like.

The compounds of formula I can be converted into acid addition salts, particularly those which can be used in pharmaceutical preparations, by treatment with inorganic acids such as hydrochloric acid, sulfuric acid, phosphoric acid, or the like, or organic acids such as formic acid, acetic acid, succinic acid, lactic acid, citric acid, maleic acid, fumaric acid, tartaric acid, methanesulfonic acid, p-toluenesulfonic acid, or the like.

The benzylpyrimidine derivatives provided by the present invention, that is, the compounds of formula I and their acid addition salts, possess antibacterial activity. They inhibit the bacterial dihydrofolate reductase and potentiate the antibacterial activity of sulfonamides such as, for example, sulfisoxazole, sulfadimethoxine, sulfamethoxazole, 4-sulfanilamido-5,6-dimethoxypyrimidine, 2-sulfanilamido-4,5-dimethyl-pyrimidine, sulfaquinoxaline, sulfadiazine, sulfamonomethoxine, 2-sulfanilamido-4,5-dimethyl-isoxazole and other inhibitors for enzymes which are involved in the folic acid synthesis such as, for example, pteridine derivatives.

A combination of one or more of the benzylpyrimidine derivatives of formula I with sulfonamides can be used in a form adapted for oral, rectal or parenteral administration. The ratio of a compound of formula I to a sulfonamide can vary within a wide range; for example, in the range of from about 1:40 (parts by weight) to about 1:1 (parts by weight), the preferred ratio being in the range of from about 1:2 to about 1:10.

Thus, for example, a tablet can contain 80 mg. of a compound of formula I and 400 mg. of sulfamethoxazole, or, for example, it can contain 20 mg. of a compound of formula I and 100 mg. of sulfamethoxazole and a syrup (per 5 ml.) can contain, for example, 40 mg. of a compound of formula I and 200 mg. of sulfamethoxazole.

The benzylpyrimidine derivatives of formula I provided by the present invention possess a high antibacterial activity or a pronounced synergistic effect in combination with sulfonamides. They also have a good compatibility.

The starting materials, that is, the benzylpyrimidine derivatives of formula II, can be prepared by reacting a compound of the formula

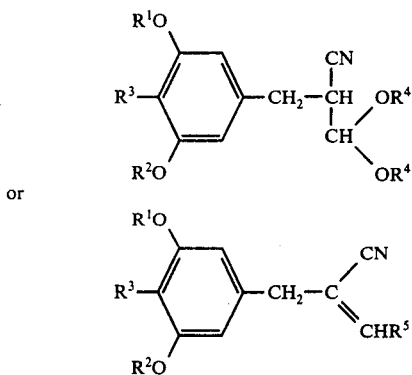

wherein $R^4$ is lower alkyl or both $R^4$'s together are lower alkylene, $R^5$ is a leaving group and $R^1$, $R^2$ and $R^3$ are as hereinbefore described,
with guanidine.

More specifically, a compound of formula IIIa or IIIb is reacted with guanidine. The symbol $R^5$ in a compound of formula IIIb is a leaving group. Exemplary of such leaving groups are ether groups, for example, lower alkoxy groups such as methoxy, ethoxy, or the like; thioether groups, for example, lower alkylthio groups; and amino groups derived from primary or secondary amines. Exemplary of such amino groups are (a) groups derived from primary aliphatic, arylaliphatic or aromatic amines, for example, (lower alkyl)amino, benzylamino and arylamino such as naphthylamino, but especiallly phenylamino (anilino), the phenyl ring optionally bearing one or more halogen, lower alkyl or lower alkoxy substituents, and (b) groups derived from secondary aliphatic, aromatic or heterocyclic amines, for example, N,N-di(lower alkyl)amino and N-(lower alkyl)-N-arylamino groups such as N-methyl-N-phenylamino (N-methylanilino), the phenyl ring optionally bearing one or more halogen, lower alkyl or lower alkoxy substituents, pyrrolidino, piperidino, piperazino, morpholino, or the like. The anilino group is an especially preferred leaving group denoted by $R^5$.

The reaction of a compound of formula IIIa or IIIb with guanidine can be carried out according to known methods, see, for example, Belgian Patent Specification Nos. 594,131; 671,982 and 746,846. Accordingly, the reaction can be carried out in a solvent, for example, an alkanol such as methanol, ethanol, or the like, dimethylformamide, dimethylsulfoxide, N-methylpyrazolone, or the like, at a temperature in the range of from about 25° C. to about 200° C., preferably in the range of from about 50° C. to about 170° C.

The compounds of formula IIIb can be formed in situ under these reaction conditions from tautomeric compounds of the formula

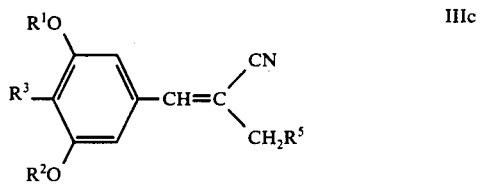

wherein $R^1$, $R^2$, $R^3$ and $R^5$ are as previously described.

The compounds of formulas IIIb and IIIc can be present as cis or trans isomers or as mixtures thereof.

In another aspect, the invention relates to 2,4-diamino-5-(4-bromo-3,5-dimethoxybenzyl)-pyrimidine which can be prepared as hereinbefore described. The 2,4-diamino-5-(4-bromo-3,5-dimethoxybenzyl)-pyrimidine forms acid addition salts with acids, which are similarly part of the invention.

The acid addition salts, especially salts usable in pharmaceutical preparations can be prepared from inorganic acids commonly used for this purpose, such as, hydrochloric acid, sulfuric acid, phosphoric acid, or the like, or organic acids commonly used for this purpose, such as, formic acid, acetic acid, succinic acid, lactic acid, citric acid, maleic acid, fumaric acid, tartaric acid, methanesulfonic acid, p-toluenesulfonic acid, or the like.

The 2,4-diamino-5-(4-bromo-3,5-dimethoxybenzyl)-pyrimidine and its salts are antibacterially active as well as active againt coccidia and plasmodia. It blocks the bacterial dihydrofolate reductase and potentiates the antibacterial, coccidiostatic and antimalarial action of sulfonamides such as, for example, sulfisoxazole, sulfadimethoxine, sulfamethoxazole, 4-sulfanilamido-5,6-dimethoxypyrimidine, 2-sulfanilamido-4,5-dimethylpyrimidine or sulfaquinoxaline, sulfadiazine, sulfamonomethoxine, 3-sulfanilamido-4,5-dimethyl-isoxazole and other inhibitors of enzymes which are associated with the folic acid biosynthesis such as, for example, pteridine derivatives.

A combination of 2,4-diamino-5-(4-bromo-3,5-dimethoxybenzyl)-pyrimidine with an aforementioned sulfonamide, for use as an antibacterial agent, can be administered in a form adapted for oral, rectal or parenteral administration. The ratio of sulfonamide can vary within a wide range, for example, it can be in the range from about 1:40 (parts by weight) to about 1:1 (parts by weight); preferred ratios are in the range of from about 1:2 to about 1:10.

Thus, for example, a tablet can contain 80 mg. of 2,4-diamino-5-(4-bromo-3,5-dimethoxybenzyl)-pyrimidine and 400 mg. of sulfamethoxazole, or, for example, it can contain 20 mg. of 2,4-diamino-5-(4-bromobenzyl)-pyrimidine and 100 mg. of sulfamethoxazole; syrup (per 5 ml.) can contain 40 mg. of 2,4-diamino-5-(4-bromobenzyl)-pyrimidine and 200 mg. of sulfamethoxazole.

The following Examples further illustrate the invention. All temperatures are in degrees Centigrade, unless otherwise mentioned.

EXAMPLE 1

Preparation of 2,4-diamino-5-(4-bromo-3,5-dimethoxybenzyl)-pyrimidine

A solution of 16.7 g. of sodium in 220 ml. of absolute methanol was treated with 200 g. of 4-bromo-3,5-dimethoxy-α-(methoxymethyl)-cinnamic acid nitrile dissolved in 110 ml. of dimethyl sulfoxide and heated on an oil bath (70° C.) until the internal temperature had reached 70° C. The mixture was stirred at this temperature for an additional 1 hour. Then, 63.5 g. of guanidine carbonate were added with stirring and the mixture was slowly heated until the internal temperature had reached 110° C. During this time, about 120 ml. of methanol had condensed in the attached water separator. The mixture was stirred at 110° C. for an additional 1 hour, then cooled to 5° C., treated with 250 ml. of water and stirred for 0.5 hour with cooling. The resulting precipitate was removed by filtration under vacuum and washed well with cold water and benzene. The crystals were triturated with about 1000 ml. of 1N hydrochloric acid, removed by filtration under suction, and the resulting 2,4-diamino-5-(4-bromo-3,5-dimethoxybenzyl)-pyrimidine hydrochloride was recrystallized from hot water (charcoal); melting point 280°–285° C.

The hydrochloride was stirred at room temperature in 400 ml. of 3N ammonium hydroxide for 30 minutes. The crystallized 2,4-diamino-5-(4-bromo-3,5-dimethoxybenzyl)-pyrimidine was removed by filtration under suction, washed well with water and dried in vacuo at 70° C. for 15 hours; melting point 234°–235° C.

The starting material was prepared as follows:

238 G. of thionyl chloride were added dropwise to a suspension of 460 g. of 4-bromo-3,5-dimethoxybenzoic acid in 1200 ml. of absolute benzene and 25 ml. of dimethylformamide and the mixture was heated at reflux for 3 hours with stirring. The resulting solution was evaporated to dryness in vacuo. The residue was dissolved twice in 100 ml. of absolute benzene and the solvent removed each time. The residue was dissolved in a small amount of benzene, the solution was filtered and then treated with low boiling petroleum ether. The precipitated acid chloride was removed by filtration under vacuum and dried; melting point 128°–130° C.

100 G. of 4-bromo-3,5-dimethoxybenzoyl chloride were dissolved in 1000 ml. of absolute xylene. 10 G. of 5% palladium/barium sulfate were added while gassing with nitrogen and the mixture was then blown out with nitrogen for an additional 10 minutes. Hydrogen was then led through the mixture with stirring at 121° C. The course of the reaction was followed by titration of the resulting hydrogen chloride. After about 6 hours (90% of the theoretical amount of hydrogen chloride had been liberated), the reaction was stopped, the suspension cooled under nitrogen and the catalyst removed by filtration under vacuum. The filtrate was concentrated to half its volume, stirred vigorously with 1.5 liters of a 40% sodium bisulfite solution for 2 hours and then left to stand overnight. The resulting thick suspension was diluted with water. The aqueous phase was washed with benzene and adjusted to pH 10 with a 50% sodium hydroxide solution with stirring and cooling. The aldehyde was removed by filtration under vacuum and dissolved in benzene. The solution was dried over magnesium sulfate, filtered and evaporated. After recrystallization from heptane, the 4-bromo-3,5-dimethoxybenzaldehyde had a melting point of 112°–113° C.

160 G. of distilled β-methoxypropionitrile and 233 g. of 4-bromo-3,5-dimethoxybenzaldehyde dissolved in 500 ml. of absolute methanol were added to a solution of 11.0 g. of sodium in 400 ml. of absolute methanol. After boiling under reflux for 3 hours, the solution (no more aldehyde was detectable) was cooled and left to stand overnight in a refrigerator. The resulting crystals were removed by filtration under suction, washed with a small amount of cold methanol and dried. After recrystallization from methanol, the 4-bromo-3,5-dimethoxy-α-(methoxymethyl)-cinnamic acid nitrile had a melting point of 113°–114° C.

EXAMPLE 2

Preparation of 2,4-diamino-5-(4-chloro-3,5-dimethoxybenzyl)-pyrimidine

21 G. of 4-chloro-3,5-dimethoxy-α-cyano-hydrocinnamaldehyde dimethyl acetal were heated to reflux for 1.5 hours with 140 ml. of a 1N methanolic guanidine solution. The solvent was then removed by distillation on an oil bath at 160° C. and the residue heated for 15–20 minutes at this temperature until completely solidified to a crystalline mass. The mass was slurried with 80–100 ml. of water and removed by filtration under suction, whereby there was obtained 2,4-diamino-5-(4-chloro-3,5-dimethoxybenzyl)-pyrimidine of melting point 218° C.

For purification, the product was dissolved in 150 ml. of acetic acid, the solution cooled and the crystallized acetate removed by filtration under suction. The crystals were dissolved in 150 ml. of hot water and the solution treated with charcoal with heating. The base was reprecipitated from the filtrate by treatment with ammonia; melting point 222°–223° C.

The starting material was prepared as follows:

227 G. of methyl acetoacetate and 196 g. of methyl crotonate were added to a solution of 45 g. of sodium in 670 ml. of methanol. The mixture was heated to reflux for 5 hours with stirring. After cooling, the sodium salt was removed by filtration from the mixture under suction. A second and third fraction of the sodium salt were obtained by concentration of the mother liquor. Acidification of a concentrated, aqueous solution of the combined sodium salt fractions with acetic acid gave 6-methyl-cyclohexadione-2,4-carboxylic acid methyl ester of melting point 126° C.

121 G. of 6-methyl-cyclohexadione-2,4-carboxylic acid methyl ester were dissolved in 650 ml. of dimethylformamide. The solution was immersed in an ice/salt mixture and treated dropwise over 2 hours with 196 g. of sulfuryl chloride with stirring at 0°–5° C. The mixture was then stirred for an additional hour at 0°–5° C. and for several hours at room temperature. The mixture was then heated to 80° C. for 2.5 hours, the solvent removed under reduced pressure on a waterbath and the residue dissolved in 700 ml. of ethyl acetate. The solution was washed twice with 300 ml. of water each time, dried over sodium sulfate and evaporated. The crystalline residue was recrystallized from 300–400 ml. of toluene and yielded 3-chloro-2,4-dihydroxy-6-methyl-benzoic acid methyl ester of melting point 122°–125° C. An analytical sample was obtained by repeated recrystallization from toluene and had a melting point of 129° C.

143 G. of 3-chloro-2,4-dihydroxy-6-methyl-benzoic acid methyl ester were heated to reflux for 30 minutes with 1 liter of a 3N sodium hydroxide solution. The mixture was acidified carefully with 400 ml. of 10N sulfuric acid and the 4-chloro-3,5-dihydroxytoluene salted out by the addition of 300–400 g. of ammonium sulfate. After extraction with ethyl acetate and evaporation of the solvent under reduced pressure, the residue was crystallized from water, whereby there was obtained 4-chloro-3,5-dihydroxytoluene, having a m.p. of 138°–139° C.

126.5 G. of 4-chloro-3,5-dihydroxytoluene were dissolved in 150 ml. of methanol and treated with 182 ml. of dimethylsulfate. A solution of 92 g. of sodium hydroxide in 180 ml. of water was then added dropwise during 45–60 minutes at 40°–45° C. with stirring. The mixture was then heated to reflux for 20 minutes. The mixture was diluted with water, extracted with ether and finally yielded 4-chloro-3,5-dimethoxytoluene having a melting point of 72° C.

77.5 G. of 4-chloro-3,5-dimethoxytoluene were dissolved in 1030 ml. of pyridine. The solution was heated to reflux and treated dropwise during 1 hour with a solution of 197 g. of potassium permanganate in 3100 ml. of hot water. The mixture was heated to reflux for an additional 30 minutes. Then, 1700 ml. of a pyridine/water mixture were recovered by distillation. The residue was removed by filtration under suction while hot and, after cooling, the filtrate was acidified with 600 ml. of 10N sulfuric acid. The precipitate was removed by filtration and extracted with ether to recover unreacted starting material, whereby there was obtained 4-chloro-3,5-dimethoxybenzoic acid having a melting point of 247° C.

97 G. of 4-chloro-3,5-dimethoxybenzoic acid, 64 g. of thionyl chloride and 3 ml. of dimethylformamide were heated to reflux for 2.5 hours. The resulting acid chloride was crystallized from 500 ml. of ligroin (boiling point 60°–120° C.) and dried over paraffin and sodalime; melting point 102°–103° C.

28 G. of the acid chloride were dissolved in 200 ml. of methylene chloride and the solution was cooled to 0°–5° C. 12 G. of triethylamine and then 5.6 g. of ethyleneimine were added dropwise at 0°–5° C. during 20 minutes while stirring. The mixture was then shaken out with water, dried over magnesium sulfate and evaporated under reduced pressure. The residue was dissolved in 300 ml. of tetrahydrofuran and reduced with 1.8 g. of lithium aluminum hydride at −5° C. to 0° C. After 45 minutes, 130 ml. of 5N sulfuric acid were added dropwise and the mixture then heated to reflux for 30 minutes, whereupon 75 g. of ammonium sulfate were added, the organic layer was separated and yielded 4-chloro-3,5-dimethoxybenzaldehyde of melting point 119° C.

A mixture of a methanolic sodium methylate solution (prepared by dissolving 1.15 g. of sodium in 100 ml. of methanol), 17 g. of β-methoxypropionitrile and 20 g. of 4-chloro-3,5-dimethoxybenzaldehyde was heated to reflux for 3.5 hours. On cooling, 3,5-dimethoxy-4-chloro-α-(methoxymethyl)-cinnamic acid nitrile crystallized, melting point 112°–113° C.

A solution of 4.6 g. of sodium in 70 ml. of methanol was treated with 3,5-dimethoxy-4-chloro-α-(methoxymethyl)-cinnamic acid nitrile. The mixture was heated to reflux for 24 hours, the reaction stopped by the addition of water and the mixture extracted with methylene chloride. The solvent was evaporated under reduced pressure and the residue crystallized from 2-propanol, whereby there was obtained 4-chloro-3,5-dimethoxy-α-cyano-hydrocinnamaldehyde dimethyl acetal of melting point 84° C.

EXAMPLE 3

Preparation of 2,4-diamino-5-(4-fluoro-3,5-dimethoxybenzyl)-pyrimidine 1.6 G. of β-methoxypropionitrile and 1.65 g. of 4-fluoro-3,5-dimethoxybenzaldehyde were dissolved in a solution of 0.11 g. of sodium metal in 15 ml. of absolute methanol and heated at reflux for 3 hours. The mixture was evaporated and the residue taken up in 50 ml. of benzene and 10 ml. of water. The aqueous phase was washed twice with 20 ml. of benzene each time. The combined benzene extracts were dried and evaporated. The resulting 4-fluoro-3,5-dimethoxy-α-(methoxymethylene)-hydrocinnamic acid nitrile was employed in the subsequent reaction.

A solution of 0.17 g. of sodium in 4 ml. of absolute methanol was treated with 1.50 g. of 4-fluoro-3,5-dimethoxy-α-(methoxymethylene)-hydrocinnamic acid nitrile dissolved in 2 ml. of dimethylsulfoxide. The mixture was heated on an oil bath at 70° C. until the internal temperature reached 70° C. The mixture was stirred for an additional hour at this temperature. 0.64 G. of guanidine carbonate were then added and the mixture slowly heated until the internal temperature had reached 110° C., during which methanol condenses in the attached water separator. After 1 hour, the mixture was cooled, treated with water and stirred for 30 minutes. The resulting precipitate was removed by filtration and washed with cold water and benzene. After recrystallization from methanol, there was obtained 2,4-dismino-5-(4-fluoro-3,5-dimethoxybenzyl)-pyrimidine of melting point 216°–220° C.

The starting material was prepared as follows:

13.8 G. of sodium were dissolved in 900 ml. of methanol. 46.8 G. of 3-hydroxy-5-keto-3-cyclohexenecarboxylic acid were added to this solution. The mixture was stirred, maintained between −4° C. and −8° C. with a cooling bath and treated over a period of 30 minutes with a phenyl diazonium chloride solution prepared from 27.9 g. of aniline, 450 ml. of water, 72 ml. of concentrated hydrochloric acid and 21.0 g. of sodium nitrite in 90 ml. of water. The mixture was stirred −5° C. to −10° C. for an additional hour. The resulting red precipitate was removed by filtration under vacuum and washed with about 1000 ml. of water, thereby there was obtained 3-hydroxy-5-keto-4-phenylazo-3-cyclohexenecarboxylic acid of melting point 218° C.

60 G. of 3-hydroxy-5-keto-4-phenylazo-3-cyclohexene-carboxylic acid, 200 ml. of methanol, 1200 ml. of benzene and 5 g. of p-toluenesulfonic acid were heated together at reflux for 18 hours on a water separator. After cooling, the solution was washed with 500 ml. of a 5% sodium bicarbonate solution, washed with water, dried and evaporated. The residue was dissolved in ethyl acetate and purified on an aluminum oxide column (500 g., activity stage I). After evaporation of the ethyl acetate, there was obtained 3-hydroxy-5-keto-4-phenylazo-3-cyclohexenecarboxylic acid methyl ester of melting point 144° C. (from benzene/petroleum ether).

54.8 G. of 3-hydroxy-5-keto-4-phenylazo-3-cyclohexene-carboxylic acid methyl ester, 12.0 g. of acetamide and 2.0 g. of bromosuccinimide were stirred in 600 ml. of chloroform and treated dropwise with 32.0 g. of bromine dissolved in 400 ml. of chloroform. The reaction temperature was kept below 35° C. Separation of acetamide hydrobromide soon began. The mixture was stirred at room temperature for an additional 30 minutes and the acetamide hydrobromide was removed by filtration. The filtrate was evaporated to dryness and the residue taken up in a small amount of ethanol, removed by filtration under vacuum and washed with ethanol, whereby there was obtained 3,5-dihydroxy-4-phenylazo-benzoic acid methyl ester of melting point 216°–218° C.

A mixture of 27.2 g. of 3,5-dihydroxy-4-phenylazobenzoic acid methyl ester, 150 ml. of methanol and 64 g. of dimethylsulfate was treated over a period of 45 minutes with a solution of 23 g. of sodium hydroxide in 50 ml. of water with stirring. Care was taken that the temperature did not exceed 55° C. with the aid of a cooling bath. The mixture was stirred at room temperature for an additional hour, cooled with ice-water, filtered under vacuum and recrystallized from 400 ml. of ethanol, whereby there were obtained red crystals of 3,5-dimethoxy-4-phenylazo-benzoic acid methyl ester; melting point 130°–132° C.

12 G. of 3,5-dimethoxy-4-phenylazo-benzoic acid methyl ester were dissolved in 400 ml. of ethanol and, after the addition of 0.80 g. of palladium on charcoal, hydrogenated at atmospheric pressure and room temperature. With slight warming, 2 mols of hydrogen were taken up in 1.5 hours. The catalyst was separated and the filtrate concentrated in vacuo. The aniline formed was removed by distillation with steam. After cooling, the 4-amino-3,5-dimethoxybenzoic acid methyl ester remaining as an aqueous suspension was filtered under vacuum, dried and recrystallized from cyclohexane; melting point 115°–116° C.

A suspension of 214 g. of dimethylsulfone and 78.2 g. of sodium hydride (50% dispersion in oil) in 400 ml. of absolute dimethylsulfoxide was stirred at 50° C. for 3 hours under nitrogen and with the exclusion of moisture. The mixture was cooled to 30° C. and 137 g. of 4-amino-3,5-dimethoxy-benzoic acid methyl ester were added, the temperature rose to 50° C. After stirring under an atmosphere of nitrogen at room temperature for about 1 hour, a viscous mass resulted which, after standing for 3 hours, was dissolved in 2 liters of water with the addition of ice. The solution was adjusted to a pH 6–7 with glacial acetic acid. After stirring for 1 hour with ice-cooling, the crystallized 4′-amino-3′,5′-dimethoxy-2-methylsulfonyl-acetophenone was removed by filtration under suction, washed with water, dried and recrystallized from ethyl acetate; melting point 166°–167° C.

A suspension of 123 g. of 4′-amino-3′,5′-dimethoxy-2-methylsulfonylacetophenone and 68 g. of sodium borohydride in 1.5 liters of alcohol was stirred at room temperature for 20 hours. The suspension was diluted with 1.5 liters of water. The alcohol was evaporated in vacuo and the remaining 4-amino-3,5-dimethoxy-α-(methylsulfonyl-methyl)-benzyl alcohol was removed by filtration under suction, washed with water and dried; melting point 178°–179° C.

138 G. of 4-amino-3,5-dimethoxy-α-(methylsulfonylmethyl)-benzyl alcohol in 250 ml. of dimethylsulfoxide were treated with 9.75 g. of sodium amide. The mixture was stirred at room temperature for 1.25 hours and then poured into 2 liters of water. The resulting precipitate was extracted with 2 liters of ethyl acetate and the aqueous phase also extracted with 2 liters of ethyl acetate. The ethyl acetate phases were washed ion-free with two 1 liter portions of water, dried over magnesium sulfate, filtered and evaporated to dryness in vacuo at 40° C. The crystalline residue was dissolved while hot in 250 ml. of methanol, the solution treated with 150 ml. of water and left to stand at 4° C. for 18 hours. The crystallized 4-amino-3,5-dimethoxybenzaldehyde was removed by filtration under suction, washed ion-free with a mixture of 40 ml. of methanol and 20 ml. of water and dried in vacuo at 50° C.; melting point 90°–93° C.

A solution of 1.4 g. of 4-amino-3,5-dimethoxybenzaldehyde in 20 ml. of 50% hydrogen tetrafluoroborate was diazotized at 0° C. with a solution of 0.59 g. of sodium nitrite in about 2 ml. of water. After irradiation with a low pressure mercury lamp (Hanau NK 6620) for 6 hours at room temperature, the solution was extracted with ether, the ether extracts dried over magnesium sulfate and concentrated. After recrystallization from heptane, the residue produced 3,5-dimethoxy-4-fluoro-benzaldehyde of melting point 97°–98° C.

EXAMPLE 4

Preparation of 2,4-diamino-5-(4-iodo-3,5-dimethoxybenzyl)-pyrimidine

Guanidine was liberated from 0.48 g. of guanidine hydrochloride by treatment with a solution of 110 mg. of sodium metal in 10 ml. of methanol. After removal of the sodium chloride by filtration under vacuum, the filtrate was treated with 0.9 g. of 4-iodo-3,5-dimethoxy-α-(methoxymethylene)-hydrocinnamic acid nitrile and the mixture heated at reflux for 5 hours. After cooling, the product was separated and recrystallized from methanol, whereby there was obtained 0.7 g. of 2,4-diamino-5-(4-iodo-3,5-dimethoxybenzyl)-pyrimidine of melting point 238°–240° C.

The starting material was prepared as follows:

A solution of 9 g. of sodium nitrite in 30 ml. of water was added dropwise (negative potassium iodide test) at 0°–5° C. to a solution of 23.9 g. of 4-amino-3,5-dimethoxybenzaldehyde in 315 ml. of 1N hydrochloric acid with stirring and the mixture stirred for an additional 10 minutes. The resulting diazonium salt was treated with a solution of 26.2 g. of potassium iodide in 15 ml. of water, stirred for 15 minutes at room temperature and for 45 minutes at 50° C. until the evolution of nitrogen ceased. After cooling, the resulting precipitate was removed by filtration under vacuum and taken up in about 1.5 liters of ether. The ethereal phase was washed with two 200 ml. portions of 2N sodium hydroxide and with three 200 ml. portions of water, dried over magnesium sulfate and evaporated. After recrystallization from hot n-heptane, the residue produced 19.2 g. of 3,5-dimethoxy-4-iodobenzaldehyde of melting point 127°–128° C.

0.84 G. of β-methoxypropionitrile were added to a solution of 70 mg. of sodium metal in 10 ml. of absolute methanol, the mixture treated with 2.9 g. of 3,5-dimethoxy-4-iodobenzaldehyde and heated at reflux for 5 hours. Then, the mixture was cooled and the precipitated 4-iodo-3,5-dimethoxy-α-(methoxymethylene)-hydrocinnamic acid nitrile recrystallized from methanol; melting point 93°–94° C.

EXAMPLE 5

Preparation of 2,4-diamino-5-(4-bromo-3,5-dimethoxybenzyl)-pyrimidine $N^1$-oxide 3.4 G. of 2,4-diamino-5-(4-bromo-3,5-dimethoxybenzyl)-pyrimidine were suspended in 40 ml. of dioxane and treated with 2.4 g. of 3-chloroperbenzoic acid with stirring. The temperature rose to 38° C. and, after 5 minutes (no more oxidizing agent was detectable), an additional 1.2 g. of 3-chloroperbenzoic acid were added. A clear solution resulted which, after stirring for 15 minutes, became cloudy. After 2 hours, the white precipitate was removed by filtration under vacuum, washed with a small amount of dioxane and recrystallized from ethanol, whereby there was obtained 2,4-diamino-5-(4-bromo-3,5-dimethoxybenzyl)-pyrimidine $N^1$-oxide of melting point 277°–278° C.

The filtrate was concentrated in vacuo. The resulting resinous residue was triturated with a small amount of methylene chloride and removed by filtration under vacuum. The crystalline material was suspended in a 5% sodium bicarbonate solution, stirred for 30 minutes, removed by filtration under suction, washed with water and dried. Recrystallization from ethanol (or benzene/petroleum ether) gave 2,4-diamino-5-(4-bromo-3,5-dimethoxybenzyl)-pyrimidine $N^3$-oxide of melting point 245°–246° C.

I claim:

1. An antibacterial pharmaceutical composition comprising an antibacterially effective amount of one part by weight of 2,4-diamino-5-(4-bromo-3,5-dimethoxybenzyl)-pyrimidine to 1 to 40 parts by weight of an antibacterially active sulfonamide and a carrier.

* * * * *